US006400792B1

(12) United States Patent
Misawa

(10) Patent No.: US 6,400,792 B1
(45) Date of Patent: Jun. 4, 2002

(54) METHOD FOR MEASURING SPEED AND HIGH RESOLUTION INFORMATION OF MOVING OBJECT BY HIGH-SPEED X-RAY CT, AND ITS DEVICE

(75) Inventor: Masaki Misawa, Tsukuba (JP)

(73) Assignee: Agency of Industrial Science and Technology, Tokyo (JP)

( * ) Notice: Subject to any disclaimer, the term of this patent is extended or adjusted under 35 U.S.C. 154(b) by 0 days.

(21) Appl. No.: 09/662,137

(22) Filed: Sep. 14, 2000

(30) Foreign Application Priority Data

Sep. 14, 1999 (JP) .......................................... 11-260133

(51) Int. Cl.[7] ................................................. A61B 6/03
(52) U.S. Cl. ................................ 378/19; 378/8; 378/20
(58) Field of Search ........................... 378/4, 8, 20, 19, 378/154; 257/686, 723

(56) References Cited

U.S. PATENT DOCUMENTS 5,423,315 A    6/1995  Margosian et al. ...... 128/653.2

6,175,611 B1   1/2001  Melen et al. .................. 378/19

FOREIGN PATENT DOCUMENTS

JP          10-295682         11/1998

*Primary Examiner*—David P. Porta
*Assistant Examiner*—Therese Barber
(74) *Attorney, Agent, or Firm*—Oblon, Spivak, McClelland, Maier & Neustadt, P.C.

(57) ABSTRACT

A single detector module is used both for CT imaging of two sections to measure the velocity of a moving object, and high spatial resolution measurement of a single section. A large number of slender CdTe devices are arranged to project alternately. Slits are aligned with sparsely arranged portions of the devices on both end sides of the devices, and the internal information of two sections of the moving object is simultaneously measured by detecting X-rays passing through the slits. The internal information of the two sections is again simultaneously measured after a very short time interval, and the speed of the moving object is obtained by comparison. A densely arranged portion of the CdTe devices can be used for high spatial resolution measurement of the object by exchanging the slits.

4 Claims, 2 Drawing Sheets

METHOD FOR MEASURING SPEED AND HIGH RESOLUTION INFORMATION OF MOVING OBJECT BY HIGH-SPEED X-RAY CT, AND ITS DEVICE

TECHNICAL FIELD OF THE INVENTION

The present invention relates to a measuring method which not only effectively enables the measurement of the velocity of a moving object by the high-speed X-ray CT, for example, the non-destructive test for industrial use (visualization of a moving body), the measurement of a multi-phase flow, the measurement of the distribution of an opaque fluid and the measurement of the cross-section distribution of the flow passage of powder transport, but also enables the high resolution profiling of an object using a same detector module, and its device.

DESCRIPTION OF THE RELATED ART

The X-ray CT is usually used to measure the density distribution in a cross section of a resting object at a standstill such as a human organ or a structure. Thus, if the object is an infant who is not resting, or if a structure is incompletely held and moves during the measurement, the signal information for image reconstruction becomes inconsistent, and the movement of the object appears as an artifact on the image. On the other hand, in the high-speed X-ray CT, the scanning speed is as high as 250 exposures a second, which is very high, and even an object moving at the velocity of about 1 m/s can be captured, and the change of the structure inside the object with time can be visualized.

However, the information generally obtained by the X-ray CT is the density distribution in the cross section, and the moving velocity can not be measured in a case where the object shape changes in time like bubbles in a liquid. This is because only a single cross section has been measured by CT, and the velocity of the deforming object must be measured by other measuring devices than the X-ray CT. For example, the high speed X-ray CT disclosed in Japanese Examined Patent Application Publication No. 5-60381 (Official Gazette) (Super-high speed X-ray CT scanner) and Japanese Unexamined Patent Application Publication No. 10-295682 (Official Gazette) (High spatial resolution high-speed X-ray CT scanner) is also served for the CT measurement of the single cross section, but can not obtain the velocity of the moving object accompanying deformation.

SUMMARY OF THE INVENTION

A technical problem of the present invention is to provide a method for measuring the velocity of a moving object by the high-speed X-ray CT which is capable of measuring the velocity of the moving object (a deformable body) at the section of measurement which can not be measured by the regular X-ray CT, and its device.

Another technical problem of the present invention is to provide a method for measuring the velocity and the high resolution profile of the moving object which is capable of using the same detector module both for two-sectional CT imaging and the high spatial resolution measurement at one section to measure the velocity of the above-described moving object by a simple means of exchanging slits, and its device.

The method for measuring the velocity of the moving object by the high-speed X-ray CT of the present invention to solve the above-described problems comprises the steps of: simultaneously measuring the internal information at two sections in the moving object using the detector module in which a large number of slender devices formed of a compact semi-conductor for detecting the X-ray are arranged alternately in a projecting manner in the direction opposite to each other so that a part of the devices on end part sides are adjacent to each other, aligning slits with device sparse arrangement portions, respectively, on both end sides of the detector module where the devices are arranged in every other interval, and detecting the X-ray irradiated from an X-ray source and passed through the two slits by the devices; simultaneously measuring the internal information at two sections in the moving object by similarly detecting the X-ray through the above-described two slits after the very short time interval; and comparing the internal information of the moving object measured through the two slits at different times with each other, and obtaining the speed of the moving object based on the time interval when the internal information is closely similar to each other and the interval between the slits.

The high resolution profiling at the single section of the object can also be obtained by aligning the slits over densely arranged portion of the device, and detecting the X-ray irradiated from an X-ray source and passed through the slits by the above-described device.

A velocity measuring technique of the moving object by the high-speed X-ray CT of the present invention comprises a detector module formed by arranging a large number of slender devices formed of a compact semi-conductor for detecting the X-ray in a projecting manner alternately in a direction opposite to each other so that a part of the devices on end part sides are adjacent to each other; slits which are aligned with sparsely arranged portion of the device on both end sides of the above-described detector module where the above-described devices are arranged in every one interval; and an operation control which compares the internal information at two section measured at different times obtained through the simultaneous measurement at two sections of the moving object by the X-ray irradiated from the X-ray source and passed through the two slits with a very short time interval, based on the above-described time interval when the internal information is closely similar to each other and the interval between the above-described slits.

Further, to obtain the high resolution information of the object, the above-described velocity measuring device may be provided with slits to be aligned with the densely arranged portion of the device, and an image picking-up means to obtain the high resolution profile of the object based on the high resolution information at the single section of the object obtained by detecting the X-ray irradiated from the X-ray source and passed through the slits in the above-described device.

In the above-described method and devices of the present invention the internal information at two sections in the moving object can be simultaneously measured by irradiating the X-ray from the same X-ray source through two slits on the device sparse arrangement portion in the detector module in which a part of the devices formed of a compact semi-conductor for detecting the X-ray are arranged adjacent to each other, and the velocity of the moving object can be obtained from the time interval of two measurements and the interval between the above-described two slits by similarly achieving the simultaneous measurement of two sections by the next X-ray irradiation after a very short time interval, comparing the measurement with the data of the existing measurement.

In addition, if the high spatial resolution measurement is necessary, only the slit is exchanged, the single slit is aligned with the densely arranged portion of the detector module, and the densely arranged portion of the device in the same detector module is irradiated with the X-ray to achieve the high resolution CT imaging at the single section of the object.

DESCRIPTION OF EMBODIMENTS

Figure 1:
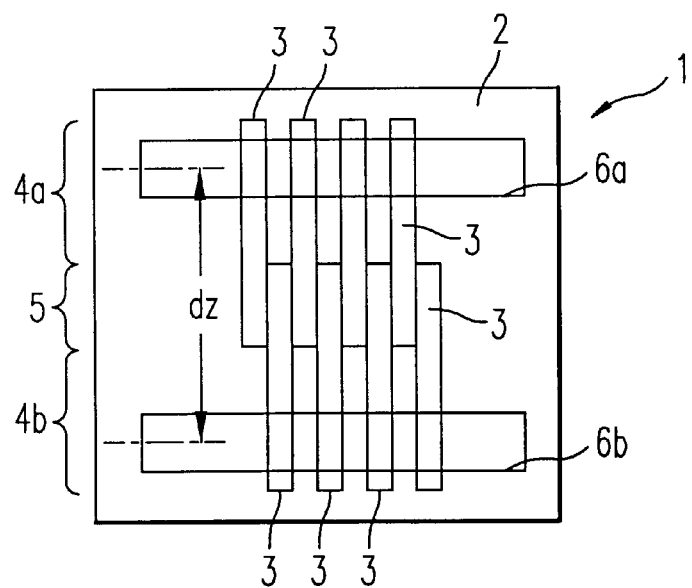
FIG. 1 is a schematic representation showing an embodiment that a detector module of the present invention is used in a velocity measurement mode.
Figure 2:
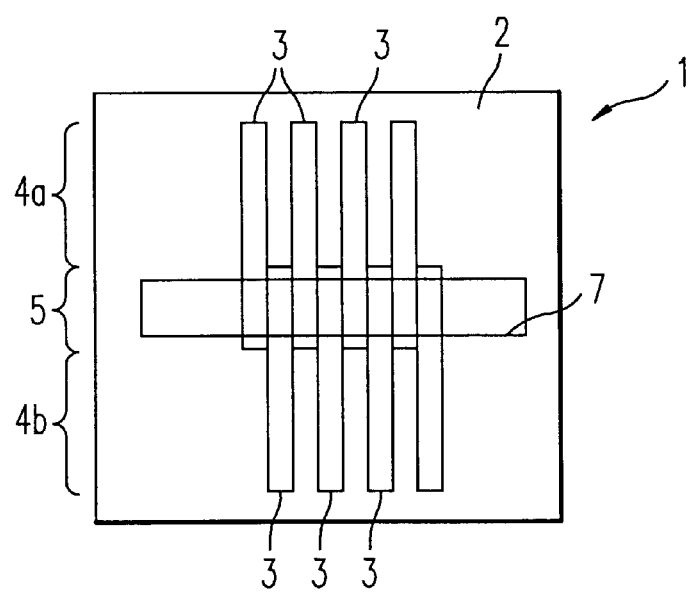
FIG. 2 is a schematic representation showing an embodiment that a detector module of the present invention is used in a high resolution mode.

FIGS. 1 and 2 show embodiments of using a detector module 1 of a semi-conductor detector for high-speed X-ray CT is used in a velocity measurement mode and a high resolution mode, respectively, in a measuring method and a measuring device of the present invention.

As shown in these figures, the detector module 1 is formed by arranging a large number of CdTe semi-conductor devices 3 machined slender and thin on a base 2 so that a part of the devices on end part sides are adjacent to each other and alternately projected in a direction opposite to each other, the above-described devices 3 are arranged on both sides of the detector module 1 in every other interval thereby, this means, two sparsely arranged portions of the device 4A and 4B whose arrangement pitch is sparse by one piece of the devices 3 are formed on both sides of a center of densely arranged portion of the device 5 in which the CdTe semi-conductor devices 3 are densely arranged.

In the velocity measurement mode as illustrated in FIG. 1, two slits 6A and 6B formed on an X-ray shielding material are aligned apart from each other by a very small distance dz with the device sparse arrangement portions 4A and 4B on both end sides of the condition detector module 1 so that the X-ray incident from an X-ray source is irradiated only on the two sparsely arranged portions of the device 4A and 4B through the slits 6A and 6B. Out of the X-rays simultaneously emitted from the X-ray source, only the X-ray passed through the slit 6A is detected at the sparsely arranged CdTe device 4A, while only the X-ray passed through the slit 6B is detected at the CdTe device sparse arrangement portion 4B. This means, the signal can be simultaneously detected at two sections of the sparsely arranged portions of the CdTe device 4A and 4B which are apart from each other by the very small distance dz on both end sides of the detector module 1.

Further, in this detector module 1, the CdTe semi-conductor devices 3 arranged adjacent to each other are separated from each other by an insulating material and independent from each other, and thus, the information on the sections from the devices 3 spaced at every other interval can be transmitted to a data collection system in the sparsely arranged portions of the CdTe device 4A and 4B, and the device 3 to detect the X-ray passed through the slit 6A is independent from the device 3 to detect the X-ray passed through the slit 6B. This arrangement enables the simultaneous measurement of the two sections.

In the next scanning by the high-speed X-ray CT after the very short time interval dt, the X-rays are similarly detected through the two slits 6A and 6B apart from each other by the very small distance dz to achieve the simultaneous measurement of the two sections in a similar manner. In comparison with the CT image by the previous scanning, the signal detected at the sparsely arranged portion of the CdTe device 4A is closely similar to the signal detected at the sparsely arranged portion of CdTe device 4B, and the velocity of a moving object can be obtained from the above-described time dt and distance dz, i.e., dz/(dt n) by identifying the n-th X-ray irradiation.

This system is ready for the velocity of the moving body in an extensive range by preparing the slits 6A and 6B different in distance dz according to the velocity of the moving body.

For this velocity measurement of the moving object, the detector module 1 is provided with an appropriate operation control procedure to obtain the velocity of the moving object by comparing the internal information of the moving object obtained by achieving the simultaneous measurement of two sections by the X-rays passed through the two slits 6A and 6B which is measured at different times, and based on the above-described time interval dt and the above-described interval dz between the slits when the internal information is closely similar to each other.

If a CT imaging of the high spatial resolution is necessary for an object, its image can be obtained in the high resolution mode as shown in FIG. 2. In the high resolution mode, the total CdTe semi-conductor devices 3 are arranged in the detector module 1, a single slit 7 is arranged so as to be aligned with the CdTe device dense arrangement portion 5, and the X-ray is irradiated on the portion where the devices 3 are densely arranged through this slit 7 to enable the measurement with high spatial resolution twice that of the previous velocity measurement.

This means, the exchange of only the slits using the same detector module 1 is ready for two modes of the velocity measurement and the high resolution.

Figure 3:
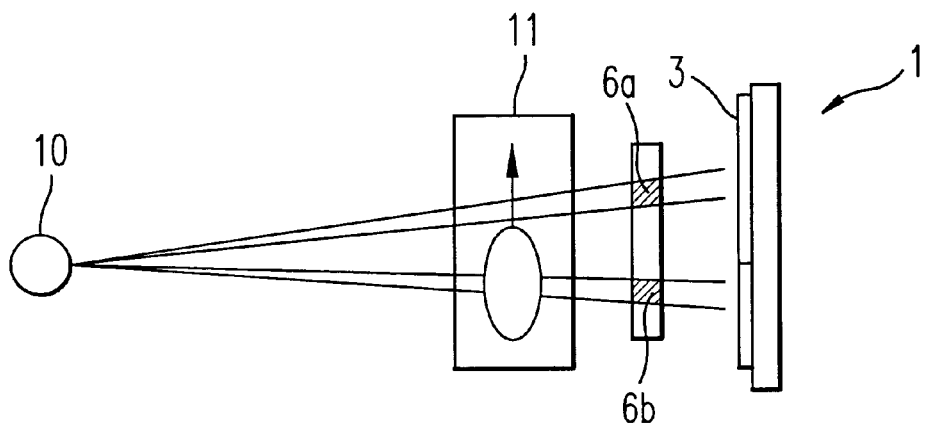
FIG. 3 is a schematic representation showing an embodiment that a detector module of the present invention is used in a velocity measurement mode.
Figure 4:
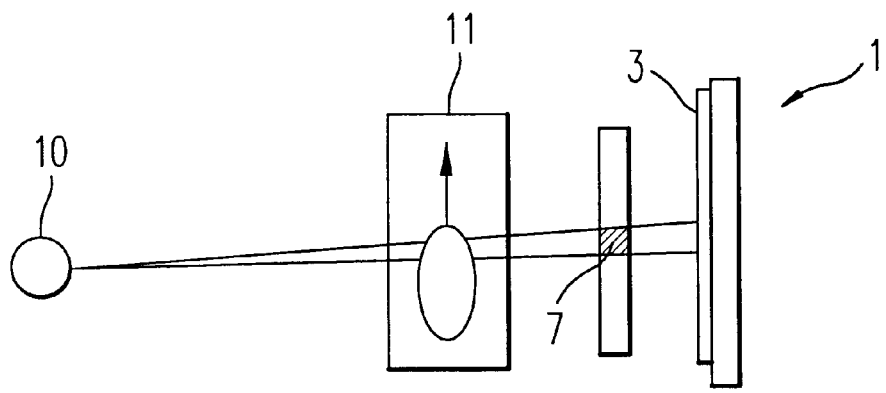
FIG. 4 is a schematic representation showing an embodiment that a detector module of the present invention is used in a high resolution mode.

FIGS. 3 and 4 are schematic representations to illustrate a service embodiment in the velocity measurement mode and the high resolution mode of the above-described semi-conductor detector for X-ray CT for single-section/double-section common use type, and shows the positional relationship of an X-ray source 10, an object 11, the slits 6A, 6B and 7, and the detector module 1.

It seems that the multi-sectional CT imaging has also been employed in the X-ray CT for medical use, but the velocity measurement of the moving body as an object is not achieved in the X-ray CT for medical use. Though there are many methods for velocity measurement using a probe, etc., unless the X-ray CT is employed, these methods are not capable of achieving the measurement over the whole section of the object.

The above-described semi-conductor detector for X-ray CT of the present invention is capable of calculating the velocity which can not be measured by conventional X-ray CT methods by arranging the compact semi-conductor devices 3 with their ends adjacent to each other, combining them with the slits 6A and 6B at two sections apart from each other by the small interval, simultaneously detecting the X-ray irradiation from the same X-ray source at two sections, and comparing the X-ray irradiation data after the very short time interval with the immediately previous data. In addition, it is also capable of achieving the high spatial resolution measurement by exchanging only the slits using the same detector module 1.

What is claimed is:

1. A method for measuring the velocity of a moving object by a high-speed X-ray CT, said method comprising the steps of, simultaneously measuring the internal information at two sections in the moving object using a detector module in which a large number of slender devices formed of a compact semiconductor for detecting the X-rays are arranged alternately in a projecting manner in the direction opposite to each other so that a part of the devices on end part sides are adjacent to each other, aligning two slits with sparsely arranged portion of the devices, respectively, on both end sides of the detector module where said devices are arranged in every other interval, and detecting the X-rays irradiated from an X-ray source and passed through said two slits by said devices;

simultaneously measuring the internal information at said two sections in the moving object by similarly detecting the X-ray through said two slits after a very short time interval; and comparing the internal information of the moving object measured through said two slits at different times with each other, and obtaining the velocity of the moving object based on the time interval when the internal information is closely similar to each other and the interval between said slits.

2. A method for measuring the high resolution profile of the moving object by the high-speed X-ray CT, said method comprising the steps of, aligning slits with a center densely arranged portion of the devices in which devices for detecting the X-rays are densely arranged in a detector module used in a method for measuring the velocity according to claim 1, and obtaining the high resolution profile at a single section of the object by detecting the X-rays irradiated from an X-ray source and passed through said slits by said devices.

3. A device for measuring the speed of a moving object by a high-speed X-ray CT comprising:

a detector module formed by arranging a large number of slender devices formed of a compact semiconductor for detecting the X-rays in a projecting manner alternately in a direction opposite to each other so that a part of the devices on end part sides are adjacent to each other;

at least two slits which are aligned on sparsely arranged portions of the devices on both end sides of said detector module where said devices are arranged in every other interval; and an operation control procedure which compares the internal information of two sections measured at different times obtained through the simultaneous measurement of said two sections of the moving object by the X-rays irradiated from the X-ray source and passed through said at least two slits with a very short time interval, based on said time interval when the internal information is closely similar to each other and the interval between said at least two slits.

4. A device for measuring the velocity of the moving object and the high resolution information by the high-speed X-ray CT according to claim 3, comprising:

said at least two slits which are aligned on a center densely arranged portion of the devices in which the devices for detecting the X-rays in the detector module are densely arranged; and an image section method to obtain the high resolution information of an object based on the high resolution information at a single section of the two sections of the object obtained by detecting the X-rays irradiated from an X-ray source and passed through said at least two slits by said devices.

* * * * *